United States Patent [19]

Ogura et al.

[11] Patent Number: 5,302,672

[45] Date of Patent: Apr. 12, 1994

[54] 2,7-DIHYDROXYNAPHTHALENE BASED EPOXY RESIN, INTERMEDIATE THEREOF, PROCESSES FOR PRODUCING THEM, AND EPOXY RESIN COMPOSITION

[75] Inventors: Ichiro Ogura; Shunji Ehara; Taku Kitamura; Hiroshi Sakata, all of Chiba, Japan

[73] Assignee: Dainippon Ink and Chemicals, Inc., Tokyo, Japan

[21] Appl. No.: 841,470

[22] Filed: Feb. 26, 1992

[30] Foreign Application Priority Data

Feb. 27, 1991 [JP] Japan .................................. 3-032765

[51] Int. Cl.$^5$ .............................................. C08G 59/08
[52] U.S. Cl. .................................... 525/481; 525/485; 525/486; 525/487; 528/89; 528/91; 528/94; 528/97; 549/560
[58] Field of Search ............... 528/97, 91, 94, 89; 525/481, 485, 486, 487

[56] References Cited

U.S. PATENT DOCUMENTS 3,391,117  7/1968  Bilow et al. ......................... 528/153
4,551,508 11/1985  Urasaki ................................ 528/97

OTHER PUBLICATIONS

Lee and Neville, "Handbook of Epoxy Resins" pp. 2–15 McGraw–Hill Inc. 1967.

*Primary Examiner*—Frederick Krass
*Attorney, Agent, or Firm*—Armstrong, Westerman, Hattori, McLeland & Naughton

[57] ABSTRACT

A 1,1-bis(2,7-diglycidyloxy-1-naphthyl)alkane as an epoxy resin; a 1,1-bis(2,7-dihydroxy-1-naphthyl)alkane as an intermediate for said epoxy resin; a process for producing said intermediate comprising reacting 2,7-dihydroxy-1-naphthalene and an aldehyde; a process for producing said epoxy resin comprising reacting said intermediate and an epihalohydrin; and an epoxy resin composition comprising said epoxy resin and a curing agent. The epoxy resin has a low melt viscosity while exhibiting excellent heat resistance.

6 Claims, 4 Drawing Sheets

PARENT PEAK: M/e = 632 ered by formula (I):
2,7-DIHYDROXYNAPHTHALENE BASED EPOXY RESIN, INTERMEDIATE THEREOF, PROCESSES FOR PRODUCING THEM, AND EPOXY RESIN COMPOSITION

FIELD OF THE INVENTION

This invention relates to a novel epoxy resin and its intermediate, a process for producing the same, and an epoxy resin composition containing said epoxy resin. More particularly, it relates to an epoxy resin which has a low melt viscosity while excellent in heat resistance, water resistance, and toughness and is therefore particularly suitable as a sealing material for semi-conductors.

BACKGROUND OF THE INVENTION

Epoxy resins, when used in combination with various curing agents, provide cured resins generally excellent in mechanical properties, water resistance, chemical resistance, and electrical properties and find their use in various fields such as adhesives, coatings, laminates, molding materials, casting materials, etc. In particular, their excellent characteristics and economical considerations have made them widely useful in semi-conductor sealing compounds.

Known epoxy resins include those produced by reacting epichlorohydrin with a novolak obtained by the reaction between 1,6-dihydroxynaphthalene and formaldehyde as disclosed in JP-A-2-227418, JP-A-61-69826, and JP-A-2-189326 (the term "JP-A" as used herein means an "unexamined published Japanese patent application").

However, since the reaction product between 1,6-dihydroxynaphthalene and formaldehyde is a mixture comprised of dimer, trimer, and other oligomers, the epoxy resin obtained by reacting such a mixture with an epihalohydrin is necessarily a mixture comprised of a dimeric epoxy resin, a trimeric epoxy resin, a tetrameric epoxy resin, a pentameric epoxy resin, etc. Such a mixed epoxy resin, though excellent in heat resistance, has a considerably high melt viscosity.

SUMMARY OF THE INVENTION

In the light of this situation, the inventors have conducted extensive investigations and, as a result, unexpectedly found that 2,7-dihydroxynaphthalene shows specific reactivity in the reaction with formaldehyde to produce a dimer alone in a substantially stoichiometrical yield in spite that it has a plurality of reactive sites and that an epoxy resin obtained by reacting the dimer with an epihalohydrin has a markedly reduced melt viscosity while retaining the excellent heat resistance possessed by the conventional epoxy resin obtained by reacting 1,6-dihydroxynaphthalene with formaldehyde and reacting the resulting novolak with epichlorohydrin. It has been additionally ascertained that the epoxy resin of the present invention also exhibits excellent water resistance.

The present invention provides 1,1-bis(2,7-diglycidyloxy-1-naphthyl)alkane; 1-bis(2,7-dihydroxy-1-naphthyl)alkane; a process for producing 1,1-bis(2,7-dihydroxy-1-naphthyl)alkane comprising reacting 2,7-dihydroxy-1-naphthalene and an aldehyde; a process for producing 1,1-bis(2,7-diglycidyloxy-1-naphthyl)alkane comprising reacting 1,1-bis(2,7-dihydroxy-1-naphthyl)alkane and an epihalohydrin; and an epoxy resin composition comprising 1,1-bis(2,7-diglycidyloxy-1-naphthyl)alkane and a curing agent.

BRIEF DESCRIPTION OF THE DRAWINGS

In the accompanying drawings.

DETAILED DESCRIPTION OF THE INVENTION

Figure 1:
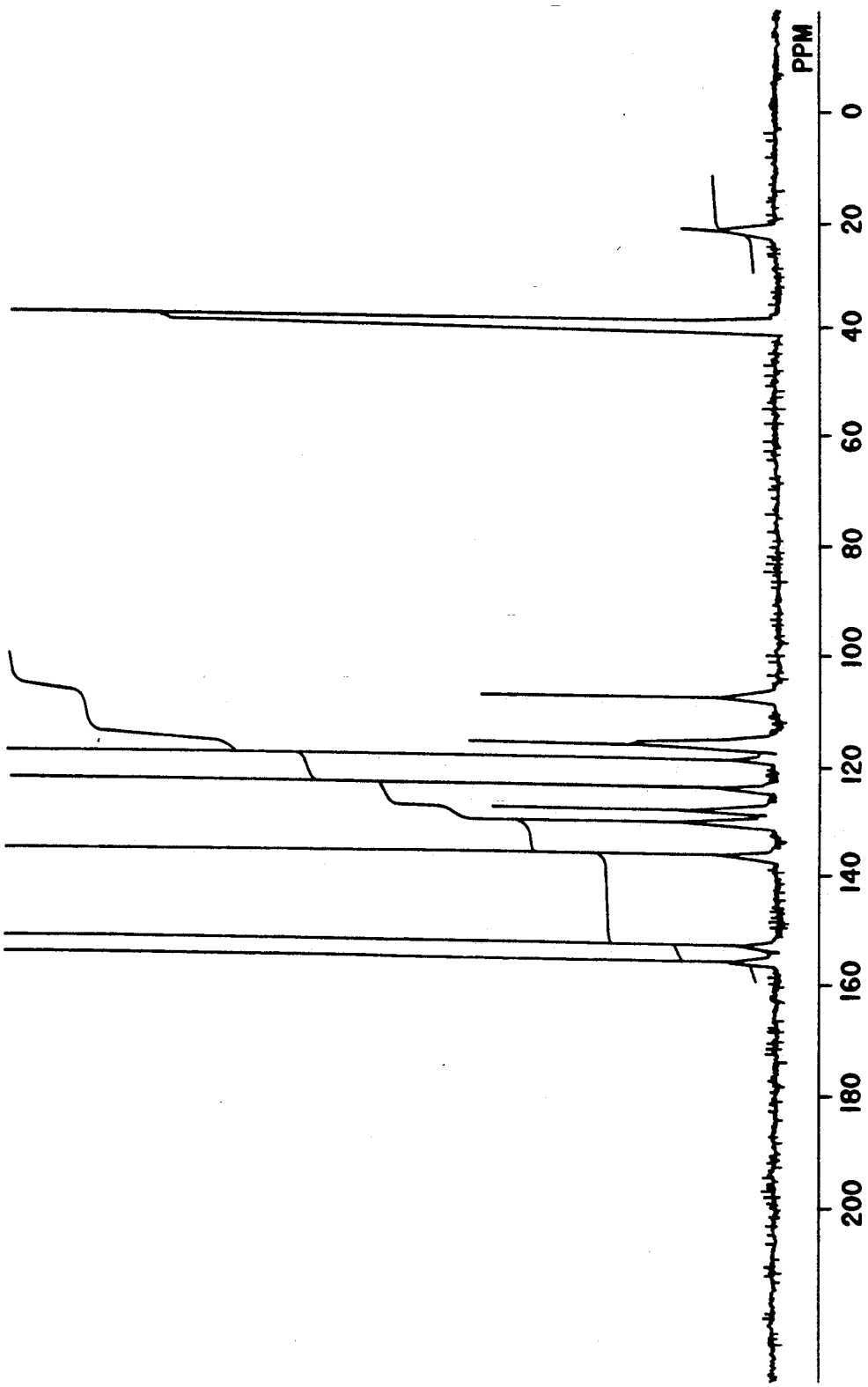
FIG. 1 is a chart showing the $^{13}C$ NMR spectra of 1,1-bis(2,7-dihydroxy-1-naphthyl)methane.

The 1,1-bis(2,7-dihydroxy-1-naphthyl)alkane, an intermediate of the epoxy resin according to the present invention, can be prepared by reacting 2,7-dihydroxynaphthalene and an aldehyde.

The 1,1-bis(2,7-dihydroxy-1-naphthyl)alkane includes those represented by formula (II):

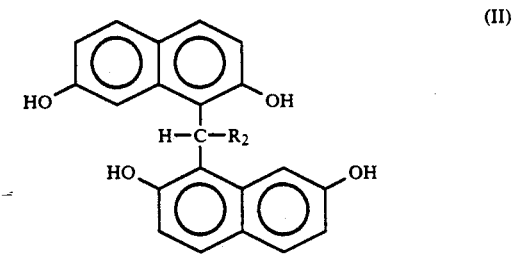

wherein $R_2$ represents a hydrogen atom, an alkyl group having 1 to 8 carbon atoms, a phenyl group, a hydroxyphenyl group, or a halogen-substituted phenyl group.

From the standpoint of heat resistance of a cured material, preferred of the compounds of formula (II) are those wherein $R_2$ is a hydrogen atom, a methyl group, an ethyl group, a propyl group, a phenyl group, or a p-hydroxyphenyl group.

The 1,1-bis(2,7-diglycidyloxy-1-naphthyl)alkane according to the present invention can be obtained by reacting the 1,1-bis(2,7-dihydroxy-1-naphthyl)alkane with an epihalohydrin.

The 1,1-bis(2,7-diglycidyloxy-1-naphthyl)alkane according to the present invention includes those represented by formula (I):

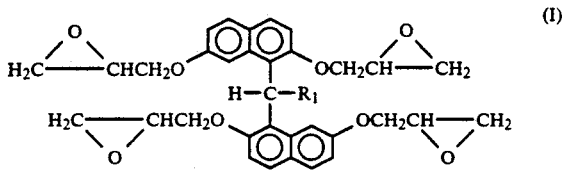

wherein $R_1$ represents a hydrogen atom, an alkyl group having 1 to 8 carbon atoms, a phenyl group, a glycidyloxyphenyl group, or a halogen-substituted phenyl group.

From the standpoint of heat resistance of a cured material, preferred of the compounds of formula (I) are those wherein $R_1$ is a hydrogen atom, a methyl group, an ethyl group, a propyl group, a phenyl group, or a p-glycidyloxyphenyl group.

The aldehydes which can be used in the present invention are not particularly limited and include formaldehyde, acetaldehyde, propyl aldehyde, butyl aldehyde, benzaldehyde, p-hydroxybenzaldehyde, and bromobenzaldehyde. From the viewpoint of heat resistance of a cured resin, preferred of these aldehydes are formaldehyde, acetaldehyde, propyl aldehyde, butyl aldehyde, benzaldehyde, and p-hydroxybenzaldehyde.

If desired, the reaction between 2,7-dihydroxynaphthalene and an aldehyde can be carried out in the presence of a catalyst. Examples of useful catalysts include basic catalysts, such as alkali metal hydroxides and alkaline earth metal hydroxides (e.g., sodium hydroxide, potassium hydroxide, lithium hydroxide, and calcium hydroxide) and alkali metal carbonates (e.g., sodium carbonate and potassium carbonate); and acidic catalysts, such as mineral acids (e.g., sulfuric acid, hydrochloric acid, nitric acid, hydrobromic acid, and perchloric acid), sulfonic acids (e.g., p-toluenesulfonic acid and benzenesulfonic acid), and carboxylic acids (e.g., oxalic acid, succinic acid, malonic acid, monochloroacetic acid, and dichloroacetic acid). These catalysts are used usually in an amount of from 0.01 to 0.1 mol per mol of the starting hydroxynaphthalene. The upper limit of the catalyst amount is not so critical and is appropriately selected taking it into consideration that too a large amount needs a large quantity of an acid or an alkali and extra time for neutralization.

In more detaile, the production method of dimeric naphthols are as follows.

The reaction between naphthols (including dihydroxynaphthalene) and aldehydes is carried out by using 0.5 to 1.0 mol aldehydes per naphthols, preferably 0.5 to 0.55 mol, in an aqueous dispersion with the presence of basic or acidic catalysts, at a temperature from 30 to 100° C., and preferably 60 to 80° C., for 0.5 to 3 hours with vigorous stirring. After neutralization, the dimeric naphthols are separated from the reaction mixture by filtration, washed with water. Where in using the mixture of naphthols the products are the mixture of homo- and mixed dimers. The inventors have confired that obtained compounds are not novolak resins, comprised of dimer, trimer and other oligomers, but substantially solely consist of dimers in all cases.

In the case of the products obtained from the mixture of 2,7-dihydroxynaphthalene and β-naphthol, dimeric mixture comprised of 1,1-bis(2,7-dihydroxy-1-naphthyl)alkane of formula (II), 1-(2,7-dihydroxy-1-naphthyl)-1-(2-hydroxyl-1-naphthyl)alkane of formula (III) and 1,1-bis(2-hydrosy-1-naphthyl)alkane of formula (IV) shown below is formed:

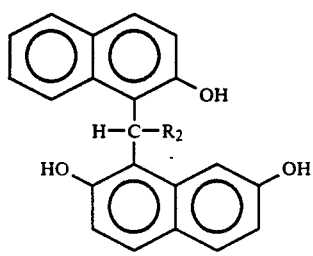

(III)

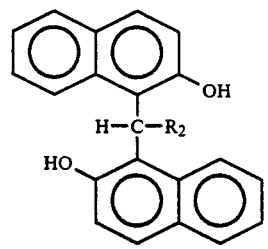

(IV)

wherein R₂ is as defined above.

In the above-mentioned reaction mode in which 2,7-dihydroxynaphthalene is used in combination with β-naphthol, the molar ratio of these naphtholic compounds is not particularly limited. As the proportion of the 2,7-dihydroxynaphthalene increases, the production ratio of the dimer of formula (II), i.e., 1,1-bis(2,7-dihydroxy-1-naphthyl)alkane, increases to obtain higher heat resistance but, in turn, the melt viscosity of the resulting epoxy resin tends to increase. On the other hand, as the proportion of β-naphthol increases, the production ratio of 1,1-bis(2,7-dihydroxy-1-naphthyl)alkane decreases and, accordingly, the production ratio of the dimer of formula (IV), i.e., 1,1-bis(2-hydroxy-1-naphthyl)alkane, increases. In the latter case, the resulting epoxy resin shows tendencies of further decreasing the melt viscosity and, in turn, of reducing heat resistance.

Therefore, with a heat resistance-viscosity balance, less liability of crystallization of the epoxy resin during epoxidation hereinafter described, and ease of production being taken into consideration, a preferred molar ratio of 2,7-dihydroxynaphthalene to β-naphthol ranges from 10/0 to 2/8.

Where 2,7-dihydroxynaphthalene is reacted with p-hydroxybenzaldehyde, there is obtained, as a dimer, 1,1-bis(2,7-dihydroxy-1-naphthyl)-4-hydroxyphenylmethane represented by formula (II'):

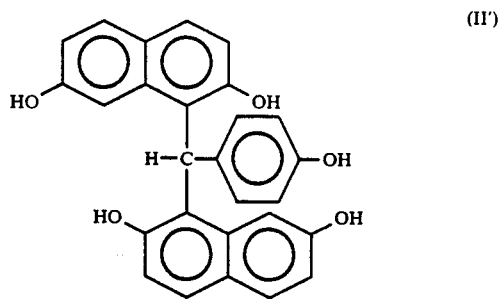

(II')

Upon being reacted with an epihalohydrin (hereinafter described), the dimer of formula (II') produces a pentafunctional epoxy resin, which gives a cured material having extremely excellent heat resistance.

Further, where a combination of 2,7-dihydroxynaphthalene and β-naphthol is reacted with p-hydroxybenzaldehyde, there is obtained, in addition to the dimer of formula (II'), 1-(2,7-dihydroxy-1-naphthyl)-1-(2-hydroxy-1-naphthyl)-1-(4-hydroxyphenyl)methane represented by formula (III'), 1,1bis(2-hydroxynaphythyl)-4-hydroxyphenylmethane represented by formula (IV'):

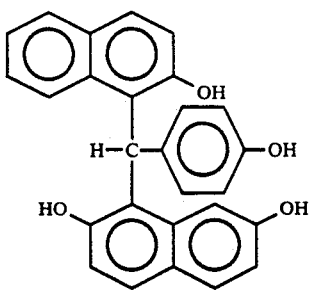

(III')

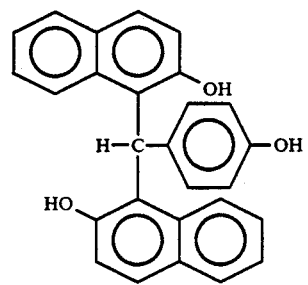

(IV')

Thus, a desired dimer or dimers can be obtained in a production ratio of substantially 100% by selecting the starting hydroxynaphthalene compound or compounds.

In short, one can obtain a dimer(s) of a hydroxynaphthalene nucleus without forming novolak molecules by choosing 2,7-dihydroxynaphthalene either alone or in combination with β-naphthol from among a number of hydroxynaphthalene compounds.

The fact that 2,7-dihydroxynaphthalene produces only a dimer without forming novolak molecules in spite of its plural reactive sites is the first finding reached by the present inventors.

In addition, the 1,1-bis(2,7-dihydroxy-1-naphthyl)alkane according to the present invention also serves as a curing agent for epoxy resins. Cured resins obtained by using this compound as a curing agent have extremely high heat resistance.

The epoxy resin according to the present invention, i.e., 1,1-bis(2,7-diglycidyloxy-1-naphthyl)alkane can be produced by epoxidation of the above-described 1,1-bis(2,7-dihydroxy-1-naphthyl)alkane. The method for epoxidation is not particularly restricted, and any method commonly employed for the production of glycidyl ethers from mono- or polyhydric phenols can be adopted.

For example, an epihalohydrin is added to the 1,1-bis(2,7-dihydroxy-1-naphthyl)alkane in an amount of from 1.5 to 20 mols, and preferably from 3.0 to 10.0 mols, per mol of the hydroxyl group of the latter compound, and the mixture is subjected to epoxidation in the presence of a base at 20 to 120° C., and preferably 50 to 80° C., for 2 to 7 hours.

The base to be used for epoxidation is not particularly limited. Examples of useful bases are potassium hydroxide, sodium hydroxide, barium hydroxide, magnesium oxide, sodium carbonate, and potassium carbonate, with potassium hydroxide and sodium hydroxide being preferred.

Examples of useful epihalohydrins are epichlorohydrin, epibromohydrin, and β-methylepichlorohydrin. In view of industrial availability, epichlorohydrin is preferred.

The molecular weight, epoxy equivalent, and melt viscosity of the resulting epoxy resin can be controlled by adjusting the molar excess ratio of epihalohydrin to the hydroxyl group of the 1,1-bis(2,7-dihydroxy-1-naphthyl)alkane. The lower the molar excess ratio of the epihalohydrin, the higher the molecular weight of the epoxy resin, and vise versa. An increase in molecular weight is accompanied by increases in epoxy equivalent and melt viscosity and, accordingly, heat resistance of the cured material obtained therefrom tends to be reduced. It should be noted, however, that changes of the molecular weight, epoxy equivalent and melt viscosity generally become inconsiderable if the molar excess ratio of epihalohydrin exceeds 10 times. Therefore, to use an epihalohydrin in an excess larger than necessary is unfavorable from the economical considerations.

The epoxy resin composition according to the present invention can be easily obtained by mixing the above-described 1,1-bis(2,7-diglycidyloxy-1-naphthyl)alkane as an epoxy resin and a curing agent.

A reaction product between a dimeric mixture of 1,1-bis(2,7-dihydroxy-1-naphthyl)alkane, 1-(2,7-dihydroxy-1-naphthyl)-1-(2-hydroxy-1-naphthyl)alkane, and 1,1-bis(2-hydroxy-1-naphthyl)alkane and epihalohydrin may also be used as an epoxy resin. Such a dimeric mixture includes a mixture of the three compounds separately synthesized and a reaction product obtained by reacting a mixture of 2,7-dihydroxynaphthalene and β-naphthol with an aldehyde as stated above. The latter mixture is preferred in view of simplified production steps.

In cases where the above-mentioned dimeric mixture is used as an epoxy resin intermediate, a variety of phenolic compounds can be used depending on the kind of the aldehyde used. For example, where the above-mentioned preferred aldehyde, i.e., formaldehyde, acetaldehyde, propyl aldehyde, butyl aldehyde, benzaldehyde, or p-hydroxybenzaldehyde is used, the resulting dimeric mixture consists of 1,1-bis(2,7-dihydroxy-1-naphthyl)alkanes selected from the group consisting of 1,1-bis(2,7-dihydroxy-1-naphthyl)methane, 1,1-bis(2,7-dihydroxy-1-naphthyl)ethane, 1,1-bis(2,7-dihydroxy-1-naphthyl)propane, 1,1-bis(2,7-dihydroxy-1-naphthyl)butane, 1,1-bis(2,7-dihydroxy-1-naphthyl)-1-phenylmethane, and 1,1-bis(2,7-dihydroxy-1-naphthyl)-1-(4-hydroxyphenyl)methane; 1-(2,7-dihydroxy-1-naphthyl)-1-(2-hydroxy-1-naphthyl)alkanes selected from the group consisting of 1-(2,7-dihydroxy-1-naphthyl)-1-(2-hydroxy-1-naphthyl)methane, 1-(2,7-dihydroxy-1-naphthyl)-1-(2-hydroxy-1-naphthyl)ethane, 1-(2,7-dihydroxy-1-naphthyl)-1-(2-hydroxy-1-naphthyl)propane, 1-(2,7-dihydroxy-1-naphthyl)-1-(2-hydroxy-1-naphthyl)butane, 1-(2,7-dihydroxy-1-naphthyl)-1-(2-hydroxy-1-naphthyl)-1-phenylmethane, and 1-(2,7-dihydroxy-1-naphthyl)-1-(2-hydroxy-1-naphthyl)-1-(4-hydroxyphenyl)methane; and 1,1-bis(2-hydroxy-1-naphthyl)alkanes selected from the group consisting of 1,1-bis(2-hydroxy-1-naphthyl)methane, 1,1-bis(2-hydroxy-1-naphthyl)ethane, 1,1-bis(2-hydroxy-1-naphthyl)propane, 1,1-bis(2-hydroxy-1-naphthyl)butane, 1,1-bis(2-hydroxy-1-naphthyl)-1-phenylmethane, and 1,1-bis(2-hydroxy-1-naphthyl)-(4-hydroxyphenyl)methane.

In this case, the resulting epoxy resin is a mixture of 1,1-bis(2,7-diglycidyloxy-1-naphthyl)alkanes selected from the group consisting of 1,1-bis(2,7-diglycidyloxy-1-naphthyl)methane, 1,1-bis(2,7-diglycidyloxy-1-naphthyl)ethane, 1,1-bis(2,7-diglycidyloxy-1-naphthyl)propane, 1,1-bis(2,7-diglycidyloxy-1-naphthyl)butane, 1,1-bis(2,7-diglycidyloxy-1-naphthyl)-1-phenylmethane, and 1,1-bis(2,7-diglycidyloxy-1-naphthyl)-1-(4-glycidyloxyphenyl)methane; 1-(2,7-diglycidyloxy-1-naphthyl)-1-(2-glycidyloxy-1-naphthyl)alkanes selected from the group consisting of 1-(2,7-diglycidyloxy-1-naphthyl)-1-(2-glycidyloxy-1-naphthyl)methane, 1-(2,7-diglycidyloxy-1-naphthyl)-1-(2-glycidyloxy-1-naphthyl)ethane, 1-(2,7-diglycidyloxy-1-naphthyl)-1-(2-glycidyloxy-1-naphthyl) propane, 1-(2,7-diglycidyloxy-1-naphthyl)-1-(2-glycidyloxy-1-naphthyl)butane, 1-(2,7-diglycidyloxy-1-naphthyl)-1-(2-glycidyloxy-1-naphthyl)-1-phenylmethane, and 1-(2,7-diglycidyloxy-1-naphthyl)-1-(2-glycidyloxy-1-naphthyl)-1-(4-glycidyloxyphenyl)methane; and 1,1-bis(2-glycidyloxy-1-naphthyl)alkanes selected from the group consisting of 1,1-bis(2-glycidyloxy-1-naphthyl)methane, 1,1-bis(2-glycidyloxy-1-naphthyl)ethane, 1,1-bis(2-glycidyloxy-1-naphthyl)propane, 1,1-bis(2-glycidyloxy-1-naphthyl)butane, 1,1-bis(2-glycidyloxy-1-naphthyl)-1-phenylmethane, and 1,1-bis(2-glycidyloxy-1-naphthyl)-1-(4-glycidyloxyphenyl)methane.

If desired, the epoxy resin composition according to the present invention may further contain other known epoxy resins in addition to the epoxy resins of the present invention.

The curing agents which can be used in the epoxy resin composition are not particularly limited, and any of compounds commonly employed as curing agents for epoxy resins can be used.

Useful curing agents include aliphatic polyamines, e.g., triethylenetetramine; alicyclic polyamines, e.g., bis(3-methyl-4-aminocyclohexyl)methane; aromatic polyamines, e.g., diaminodiphenylmethane and diaminodiphenylsulfone; phenolic novolaks; polybasic acid anhydrides, e.g., methylhexahydrophthalic anhydride and benzophenonetetracarboxylic acid dianhydride; polyamide-amine resins and modified products thereof; and latent curing agents, e.g., imidazole, dicyandiamide, boron trifluoride-amine complexes, and guanidine derivatives. Preferred of them are diaminodiphenylmethane, diaminodiphenylsulfone, phenolic novolaks, dicyandiamide, and polybasic acid anhydrides. These curing agents may be used either individually or in combination of two or more thereof.

The curing agent is usually used in such an amount that the number of amino or imino groups, active hydrogen sites (e.g., phenolic hydroxyl groups), or acid anhydride groups contained in the curing agent may approximate to the number of epoxy groups per epoxy resin molecule.

If desired, a curing accelerator may be used appropriately in combination with the curing agent. Any of compounds generally used for curing acceleration of epoxy resins may be used. Examples of suitable curing accelerators include tertiary amines, e.g., dimethylbenzylamine; imidazole compounds, e.g., 2-methylimidazole; and organophosphorus compounds, e.g., triphenylphosphine.

If desired, the epoxy resin composition according to the present invention may furthermore contain various known additives, such as fillers, colorants, flame retardants, mold release agents, and silane coupling agents.

Typical examples of useful fillers are silica powder, zirconium silicate, alumina, calcium carbonate, quartz powder, zirconium oxide, talc, clay, barium sulfate, asbestos powder, and milled glass. Useful colorants typically include carbon black. Useful flame retardants typically include antimony trioxide. Useful mold release agents typically include carnauba wax. Useful silane coupling agents typically include aminosilane and epoxysilane.

The epoxy resin composition according to the present invention has a considerably reduced melt viscosity while exhibiting excellent heat resistance. It is also excellent in water resistance and toughness. The low melt viscosity of the epoxy resin composition permits compounding of a large amount of fillers. This is particularly advantageous for application to semi-conductor elements in which the stress of a cured material should be minimized. That is, compounding of an increased amount of fillers brings the linear expansion coefficient of a cured epoxy resin close to that of a semi-conductor element.

Besides applicable to semi-conductor elements, the epoxy resin composition of the invention is suitable as an electrical insulating compound for electrical and electronic parts, e.g., a sealing material, an insulating varnish, a laminated sheet, and an insulating powder coating; a laminated sheet or a prepreg of printed circuit boards, a conductive adhesive material and a structural material, e.g., a honeycomb-panel; a fiber-reinforced plastic using various reinforcing fibers, e.g., glass fiber, carbon fiber, and aramid fiber, and a prepreg thereof; a resist ink; and the like.

As previously stated, the reaction product between 1,6-dihydroxynaphthalene and formaldehyde contains not only a dimer (i.e., 1,1-bis(1,6-dihydroxy-1-naphthyl)methane) but other polynucleic compounds, i.e., a trimer, a tetramer, etc. However, the dimer content is only 15% by weight at the most based on the total solids content, and it is very difficult to isolate the dimer from the plural polynucleic compounds even with various purification techniques. What was aimed at by the inventors is not to isolate the dimer from the plural polynucleic compounds but to develop a process for synthesizing only the purposed dimer at a production ratio of substantially 100%. It is emphasized here again that the epoxy-novolak resin obtained from a dihydroxynaphthalene disclosed in JP-A-61-69826 has 2.2 or 2.4 naphthalene nuclei as described in the working example and is, in general, a mixture of several polynucleic condensates different in the number of nuclei, i.e., a dimeric epoxy resin, a trimeric epoxy resin, a tetrameric epoxy resin, etc. As a result, a cured material obtained from this epoxy resin, though excellent in heat resistance, has a very high viscosity and is therefore inferior in workability and moldability. In particular, such a high viscosity has been a bar to use as a semi-conductor sealing material as long as current molding techniques are followed. Moreover, the high viscosity has made it impossible to compound with a large quantity of fillers, permitting no adoption of the most effective means for reducing a linear expansion coefficient. Additionally, toughness of the known epoxy resin is also unsatisfactory.

Another known epoxy resin obtained by starting with a dimer of β-naphthol connected via a methylene linkage has insufficient heat resistance because of its bifunctionality. Besides, this epoxy resin is very difficult to produce since it undergoes crystallization during epoxidation due to its vigorous crystallizing properties.

To the contrary, the 1,1-bis(2,7-diglycidyloxy-1-naphthyl)alkane of the present invention has a naphthalene skeleton serving for heat resistance and hydrophobic properties, has tetrafunctionality to achieve a high crosslinking density, and has a molecular structure of high symmetry. For these reasons, a cured material of the epoxy resin according to the present invention possesses extremely excellent heat resistance and water resistance. For example, as compared with a cured material of an epoxy-orthocresol-novolak resin (hereinafter abbreviated as ECN) whose melt viscosity is equal to that of the epoxy resin of the present invention, a cured material of the epoxy resin of the invention has a glass transition temperature 90° C. higher and a water absorption about 40% lower.

Differing from the conventional novolak type, the epoxy resin of the invention is not only excellent in toughness but satisfactory in workability and moldability owing to its low melt viscosity, e.g., about 3 ps at 150° C.

On account of the low melt viscosity, a large quantity of fillers can be compounded with the epoxy resin of the invention to thereby achieve reduction of linear expansion coefficient, which means is effective to reduce the stress when the compound is used as a semi-conductor sealing material. In addition, in spite of its high structural symmetry, the epoxy resin undergoes no crystallization during epoxidation, thus eliminating the production problem.

A cured material of the epoxy resin comprising three kinds of dimers, i.e., 1,1-bis(2,7-diglycidyloxy-1-naphthyl)alkane, 1-(2,7-diglycidyloxy-1-naphthyl)-1-(2-glycidyloxy-1-naphthyl)alkane, and 1,1-bis(2-glycidyloxy-naphthyl)alkane, has a further reduced melt viscosity while similarly exhibiting excellent heat resistance and water resistance. For instance, where 2,7-dihydroxynaphthalene and $\beta$-naphthol are used at an equimolar ratio, the resulting mixed epoxy resin consisting of 1,1-bis(2,7-diglycidyloxy-1-naphthyl)methane, 1-(2,7-diglycidyloxy-1-naphthyl)-1-(2-glycidyloxy-1-naphthyl)methane, and 1,1-bis(2-glycidyloxy-1-naphthyl)methane has a melt viscosity of 1 ps or lower at 150° C. A glass transition temperature of a cured material of this particular epoxy resin is 40° lower than that of a cured material of the 1,1-bis(2,7-diglycidyloxy-1-naphthyl)methane by about 50° C. but is still higher than that of a cured material of ECN with the melt viscosity being equal by 50° C. or more. A water absorption is about 40% lower than that of a cured material of the ECN. The further decreased melt viscosity allows addition of a larger quantity of fillers to further reduce the linear expansion coefficient. Crystallization during epoxidation can be avoided by controlling the 2,7-dihydroxynaphthalene to $\beta$-naphthol molar ratio.

Hence, the epoxy resin according to the present invention has a low melt viscosity while satisfying all the characteristic requirements of heat resistance, water resistance, and toughness and therefore provides a cured material extremely excellent in heat resistance and moisture resistance. The cured material additionally exhibits excellent toughness thus eliminating such drawbacks as hardness and brittleness generally observed with conventional highly heat-resistant epoxy resin cured materials.

In addition, the low melt viscosity of the epoxy resin of the present invention promises satisfactory workability and moldability and also permits compounding of a large quantity of fillers so as to have a reduced linear expansion coefficient.

Accordingly, the epoxy resin composition of the present invention assures high performance, high reliability, and satisfactory workability or moldability when applied to the above-mentioned various uses. The epoxy resin composition is particularly reliable in soldering temperature resistance and impact resistance when used as a sealing material for highly integrated and large-sized semi-conductor tips mounted on a surface-mounted package.

The present invention is now illustrated in greater detail with reference to Synthesis Examples and Examples in view of Comparative Examples. All the parts, percents, and ratios are by weight unless otherwise indicated. In these examples, measurements of mass spectrum and $C^{13}$-NMR spectrum were made under the following conditions.

Mass Spectrum

Mass spectrometer: Shimazu Mass Spectrometer DKB-9000
Ion Source: EI mode
Elect. Energy: 40 eV
Elect. Current: 60 $\mu$A $C^{13}$-NMR Spectrum NMR spectrometer: JEOL GSX-270 FT NMR Spectrometer

SYNTHESIS EXAMPLE 1

Tetrahydric Phenol and Epoxidized Product Thereof

In a 2 l flask equipped with a thermometer, a condenser, a dropping funnel, and a stirrer, 160 g (1 mol) of 2,7-dihydroxynaphthalene was dispersed in 1600 g of water. To the aqueous dispersion was added 4.1 g (0.05 mol) of a 49% sodium hydroxide aqueous solution at 40° C. To the mixture was added dropwise 40.2 g of a 41% formaldehyde aqueous solution (formaldehyde content: 0.55 mol) from the dropping funnel over a period of 0.5 hour while raising the temperature up to 80° C. After the dropwise addition, the mixture was kept at 80° C. for an additional one hour, and 5.1 g of 36% hydrochloric acid was added thereto to neutralize. The reaction product was separated by filtration, washed with warm water, and dried to obtain 160 g of a product. The product was found to have a crystal state at room temperature and a melting point of 253° C. Gel permeation chromatography (hereinafter abbreviated as GPC) of the product revealed a purity of 99%.

The result of measurement of $C^{13}$-NMR spectrum is shown in FIG. 1.

From these analytical results the product was identified to be 1,1-bis(2,7-dihydroxy-1-naphthyl)methane.

A 83 g aliquot (0.25 mol) of the 1,1-bis(2,7-dihydroxy-1-naphthyl)methane was dissolved in 463 g (5 mol) of epichlorohydrin, and 220 g of a 20% sodium hydroxide aqueous solution was added thereto dropwise over 5 hours at 80° C. while stirring. After keeping the mixture at that temperature for 1 hour, the aqueous phase separated was discarded. The residual phase was distilled to recover the excess epichlorohydrin, and the residue was uniformly dissolved in 210 g of methyl isobutyl ketone. The solution was washed with 70 g of water for oil water separation. Water was removed from the oily phase through azeotropic distillation, and the residue was filtered. The methyl isobutyl ketone was then removed by distillation to recover 128 g of an epoxy resin which was solid at room temperature. The resulting epoxy resin was designated (A). Epoxy resin (A) had a softening point of 96° C., a melt viscosity of 3 ps at 150° C., and an epoxy equivalent of 159.

Figure 2:
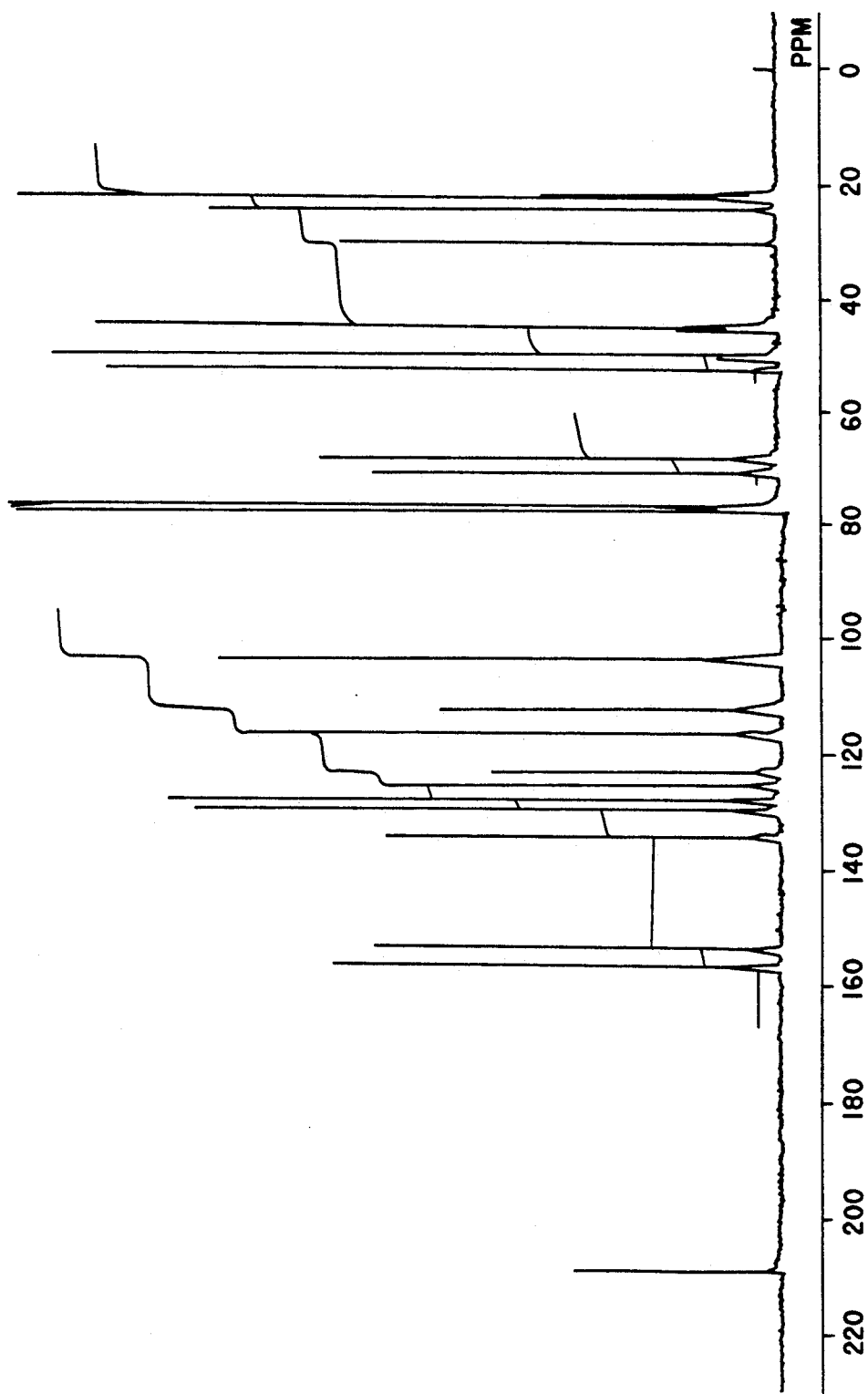
FIG. 2 is a chart showing the $^{13}C$ NMR spectra of 1,1-bis(2,7-diglycidyloxy-1-naphthyl)methane.
Figure 3:
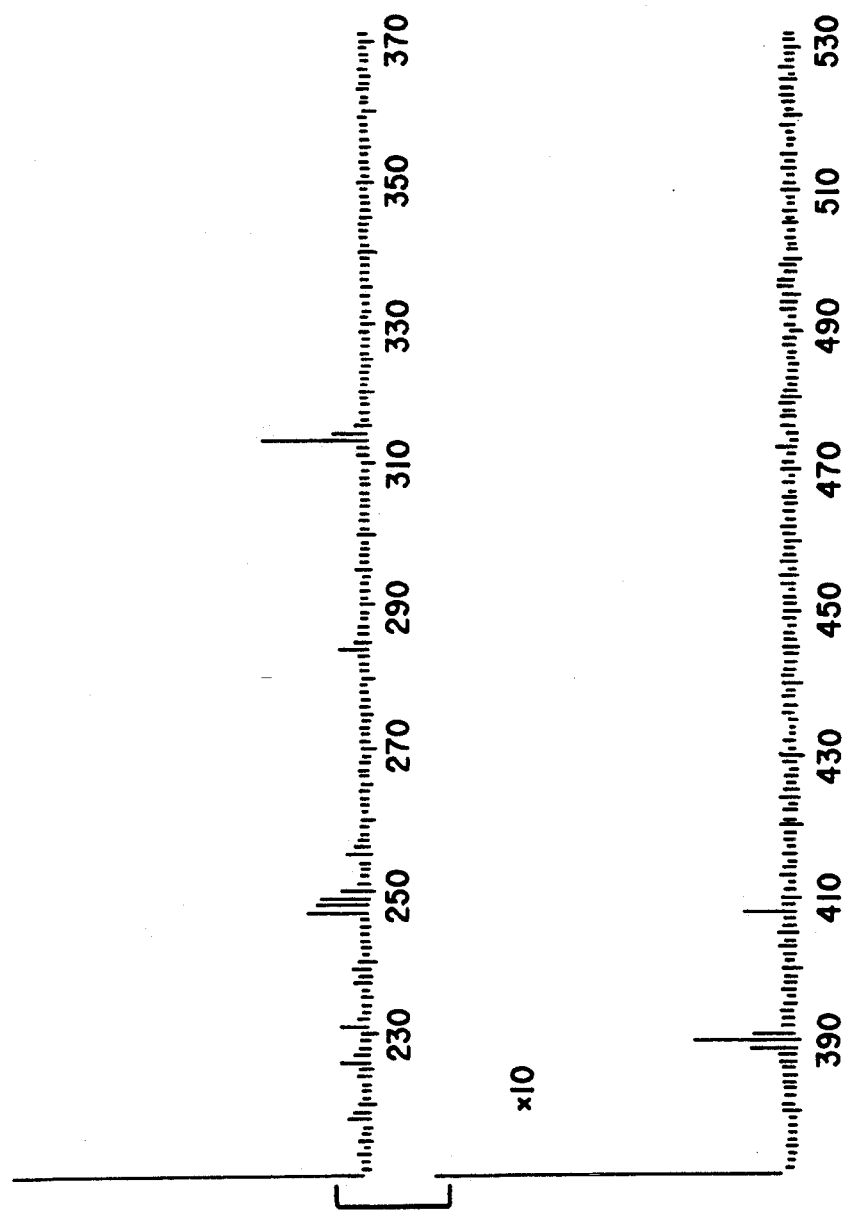
FIG. 3 is a chart showing the mass spectra of 1,1-bis(2,7-dihydroxy-naphthyl)-1-phenylmethane.
Figure 4:
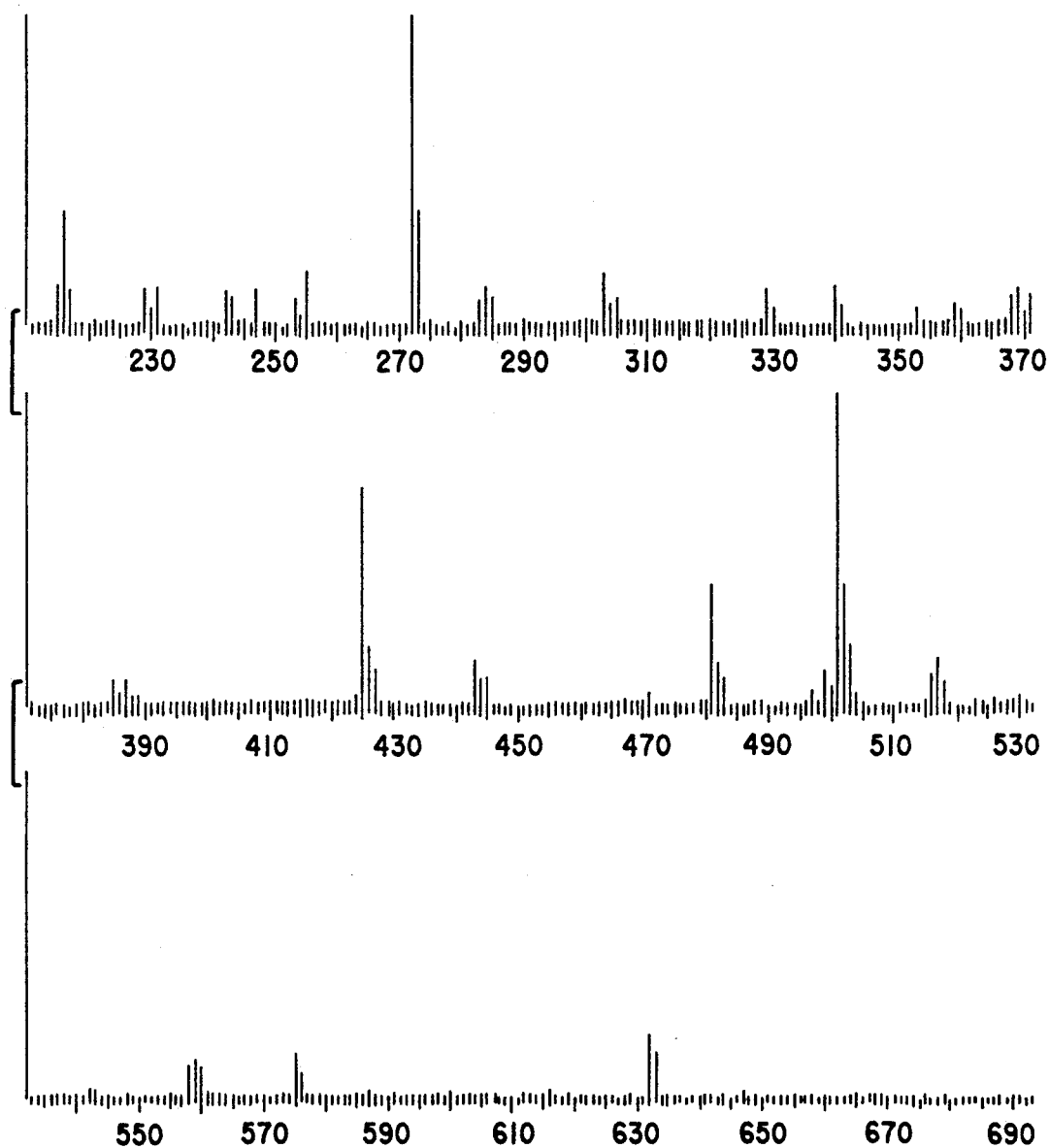
FIG. 4 is a chart showing the mass spectra of 1,1-bis(2,7-diglycidyloxy-naphthyl)-1-phenylmethane.

The result of measurement of $C^{13}$-NMR spectrum of epoxy resin (A) is shown in FIG. 2.

From these analytical results the product (A) was identified to be 1,1-bis(2,7-diglycidyloxy-1-naphthyl)methane.

SYNTHESIS EXAMPLE 2

The same procedure of Synthesis Example 1 was repeated, except for using 47.3 g of n-butyl aldehyde in place of 40.2 g of the 41% formaldehyde aqueous solution and the reaction after the addition of the sodium hydroxide aqueous solution was conducted for 5 hours at 80° C., to obtain 176 g of 1,1-bis(2,7-dihydroxy-1-naphthyl)pentane.

Epoxidation of the product with epichlorohydrin was carried out in the same manner as in Synthesis Example 1 to obtain 220 g of the corresponding epoxy compound, i.e., 1,1-bis(2,7-diglycidyloxy-1-naphthyl)pentane. The resulting epoxy resin (designated (B)) was waxy at room temperature and had a melt viscosity of 1.2 ps at 150° C. and an epoxy equivalent of 160.

SYNTHESIS EXAMPLE 3

The same procedure of Synthesis Example 1 was repeated, except for using 58.4 g of benzaldehyde in place of 40.2 g of the 41% formaldehyde aqueous solution and the reaction after the addition of the sodium hydroxide aqueous solution was conducted for 10 hours at 80° C., to obtain 198 g of polyphenol compounds mixture which contains 1,1-bis(2,7-dihydroxy-1-naphthyl)-1-phenylmethane (80 wt %) and 2,7-dihydroxynaphthalene (20 wt %).

Epoxidation of the product with epichlorohydrin was carried out in the same manner as in Synthesis Example 1 to obtain 230 g of the corresponding epoxy compound which contains 1,1-bis(2,7-diglycidyloxy-1-naphthyl)1-phenylmethane (80 wt %) and 2,7-diglycidyloxynapahthalene (20 wt %). The resulting epoxy resin (designated (C)) had a softening point of 78° C., a melt viscosity of 2.2 ps at 150° C. and an epoxy equivalent of 155.

SYNTHESIS EXAMPLE 4

Di-, Tri- and Tetrahvdric Mixed Phenol and Epoxided Product

The same procedure of Synthesis Example 1 was repeated, except for using 80 g (0.5 mol) of 2,7-dihydroxynaphthalene and 72 g of β-naphthol in place of 160 g of 2,7-dihydroxy-naphthalene, to obtain 137 g of a dimerized product. The product was found to consist of three kinds of dimers, 1,1-bis(2,7-dihydroxy-1-naphthyl)methane, 1-(2,7-dihydroxy-1-naphthyl)-1-(2-hydroxy-1-naphthyl)methane, and 1,1-bis(2-hydroxy-1-naphthyl)methane at a production ratio of 32%, 33%, and 34%, respectively, as measured by GPC.

In 463 g (5 mol) of epichlorohydrin was dissolved 105 g of the resulting product, and epoxidation reaction was carried out in the same manner as in Synthesis Example 1 to obtain 152 g of a solid epoxy resin (designated (D)). Epoxy resin (D) had a softening point of 80° C., a melt viscosity of 0.8 ps at 150° C., and an epoxy equivalent of 180.

COMPARATIVE SYNTHESIS EXAMPLE 1

A mixture of 160 g (1 mol) of 1,6-dihydroxynaphthalene, 57 g of 35% formalin, 1.8 g of oxalic acid, and 18 g of water was allowed to react under heating to 100 to 120° C. for 8 hours. Water was added to the reaction mixture, followed by heating. Water was separated by decantation, and the residue was dried at 80° C. under reduced pressure to obtain a novolak. The novolak had a 1,1-bis(1,6-dihydroxy-1-naphthyl)methane content of 5% based on the total solids content.

In 555 g (6 mol) of epichlorohydrin was dissolved 100 g of the resulting novolak, and 260 g of a 20% sodium hydroxide aqueous solution was added dropwise thereto at 80° C. over 5 hours with stirring, followed by maintaining the mixture at the same temperature for 1 hour. The aqueous phase was discarded. The residual phase was distilled to recover the excess epichlorohydrin, and the residue was uniformly dissolved in 330 g of methyl isobutyl ketone. The solution was washed with 80 g of water for oil water separation. Water was removed from the oily phase through azeotropic distillation, and the residue was filtered. The methyl isobutyl ketone was then removed by distillation to recover 155 g of an epoxy-novolak resin (designated (E)) which was solid at room temperature. Epoxy resin (E) had a softening point of 97° C., a melt viscosity of 45 ps at 150° C., and an epoxy equivalent of 159.

COMPARATIVE SYNTHESIS EXAMPLE 2

In the same manner as in Synthesis Example 1, except for replacing 2,7-dihydroxynaphthalene with 144 g (1 mol) of β-naphthol, 148 g of 1,1-bis(2-dihydroxy-1-naphthyl)methane was obtained. A 78 g aliquot of the product was dissolved in 463 g (5 mol) of epichlorohydrin, and 220 g of a 20% sodium hydroxide aqueous solution was added dropwise to the solution over 5 hours at 80° C. with stirring, followed by keeping the mixture at 80° C. for 1 hour. Meanwhile, a crystal began to precipitate, and the crystal was incorporated into the aqueous phase, making liquid separation impossible. Therefore, both aqueous and oily layers were filtered, and the filtration residue was washed with water and dried to obtain 120 g of an epoxy resin (designated (F)) as a white crystal. Epoxy resin (F) had a softening point of 174° C. and an epoxy equivalent of 145. Melt viscosity at 150° C. was unmeasurable.

EXAMPLES 1 TO 4 AND COMPARATIVE EXAMPLES 1 TO 3

Each of epoxy resins (A) to (D) obtained in Synthesis Examples 1 to 4, epoxy resins (E) and (F) obtained in Comparative Synthesis Examples 1 and 2, and ECN (softening point: 67° C., melt viscosity (150° C.): 3.2 ps; epoxy equivalent: 212) was compounded with a phenolic novolak (softening point: 80° C.) as a curing agent and triphenylphosphine as a curing accelerator at a compounding ratio shown in Table 1 below so as to have one hydroxyl group of curing agent origin per epoxy group. The resulting composition was cured at 150° C. for 2 hours and then at 180° C. for 3 hours to prepare test specimens for evaluations. Having a melting point of 174° C., epoxy resin (E) used in Comparative Example 2 failed to provide a cured material under the above-described curing conditions.

Heat resistance was evaluated by measuring a glass transition temperature (Tg) with a dynamic viscoelasticity meter (DMA), Solids Analyzer RSA-II manufactured by Rheometrics Co., under the conditions of strain: 0.02%; frequency: 1 Hz; and programming rate: 40-250° C., 30° C./min. Toughness was evaluated by measuring flexural strength, flexural modulus of elasticity, tensile strength, and tensile elongation in accordance with JIS K-6911. Water resistance was evaluated by measuring a water absorption after 9-hour boiling. The results obtained are shown in Table 1.

TABLE 1

|  | Example 1 | Example 2 | Example 3 | Example 4 | Compara. Example 1 | Compara. Example 2 | Compara. Example 3 |
|---|---|---|---|---|---|---|---|
| Composition (part): |  |  |  |  |  |  |  |
| Epoxy resin (A) | 100 | — | — | — | — | — | — |
| Epoxy resin (B) | — | 100 | — | — | — | — | — |
| Epoxy resin (C) | — | — | 100 | — | — | — | — |
| Epoxy resin (D) | — | — | — | 100 | — | — | — |
| Epoxy resin (E) | — | — | — | — | 100 | — | — |
| Epoxy resin (F) | — | — | — | — | — | 100 | — |
| ECN | — | — | — | — | — | — | 100 |
| Phenolic novolak | 65 | 57 | 66 | 64 | 65 | 71 | 49 |
| Triphenylphosphine | 0.1 | 0.1 | 0.1 | 0.1 | 0.1 | 0.1 | 0.1 |
| Melt Viscosity of Epoxy Resin (150° C.) (ps): | 3.0 | 1.2 | 2.2 | 0.8 | 45.4 | — | 3.2 |
| Results of Evaluations: |  |  |  |  |  |  |  |
| Tg (°C.) | 257 | 213 | 244 | 230 | 261 | — | 166 |
| Flexural Strength (kg/mm$^2$) | 14.2 | 12.6 | 14.1 | 15.6 | 13.3 | — | 11.5 |
| Flexural Modulus of Elasticity (kg/mm$^2$) | 275 | 279 | 293 | 258 | 397 | — | 355 |
| Tensile Strength (kg/mm$^2$) | 3.65 | 3.49 | 3.01 | 3.46 | 2.10 | — | 3.11 |
| Tensile Elongation (%) | 1.67 | 1.52 | 1.38 | 1.89 | 0.55 | — | 1.21 |
| Water Absorption After Boiling (%) | 0.36 | 0.34 | 0.33 | 0.36 | 0.77 | — | 0.63 |

The results in Table 1 prove that the cured material of the epoxy resin according to the present invention has a low melt viscosity while excellent in heat resistance, water resistance, and toughness.

Further, any of the compositions comprising the epoxy resin of the present invention and a curing agent turned out to be suitable as a semi-conductor sealing material.

While the invention has been described in detail and with reference to specific examples thereof, it will be apparent to one skilled in the art that various changes and modifications can be made therein without departing from the spirit and scope thereof.

What is claimed is:

1. An epoxy resin composition comprising a mixture of a 1,1-bis(2,7-diglycidyloxy-1-naphthyl)alkane, a 1-(2,7-diglycidyloxy-1-naphthyl)-1-(2-glycidyloxy-1-naphthyl)alkane, and a 1,1-bis(2-glycidyloxy-1-naphthyl)alkane and a curing agent.

2. An epoxy resin composition as claimed in claim 1, wherein said 1,1-bis(2,7-diglycidyloxy-1-naphthyl)alkane is selected from the group consisting of 1,1-bis(2,7-diglycidyloxy-1-naphthyl)methane, 1,1-bis(2,7-diglycidyloxy-1-naphthyl)ethane, 1,1-bis(2,7-diglycidyloxy-1-naphthyl)propane, 1,1-bis(2,7-diglycidyloxy-1-naphthyl)butane, 1,1-bis(2,7-diglycidyloxy-1-naphthyl)-1-phenylmethane, and 1,1-bis(2,7-diglycidyloxy-1-naphthyl)-1-(4-glycidyloxyphenyl)methane, said 1-(2,7-diglycidyloxy-1-naphthyl)-1-(2-glycidyloxy-1-naphthyl)alkane is selected from the group consisting of 1-(2,7-diglycidyloxy-1-naphthyl)-1-(2-glycidyloxy-1-naphthyl)methane, 1-(2,7-diglycidyloxy-1-naphthyl)ethane, 1-(2,7-diglycidyloxy-1-naphthyl)-1-(2-glycidyloxy-1-naphthyl)propane, 1-(2,7-diglycidyloxy-1-naphthyl)-1-(2-glycidyloxy-1-naphthyl)butane, 1-(2,7-diglycidyloxy-1-naphthyl)-1-(2-glycidyloxy-1-naphthyl)-1-phenylmethane, and 1-(2,7-diglycidyloxy-1-naphthyl)-1-(2-glycidyloxy-1-naphthyl)-1-(4-glycidyloxyphenyl)methane, and said 1,1-bis(2-glycidyloxy-1-naphthyl)alkane is selected from the group consisting of 1,1-bis(2-glycidyloxy-1-naphthyl)methane, 1,1-bis(2-glycidyloxy-1-naphthyl)ethane, 1,1-bis(2-glycidyloxy-1-naphthyl)propane, 1,1-bis(2-glycidyloxy-1-naphthyl)butane, 1.1-bis(2-glycidyloxy-1-naphthyl)-phenylmethane, and 1,1-bis(2-glycidyloxy-1-naphthyl)-1-(4-glycidyloxyphenyl)methane.

3. An epoxy resin composition comprising an epoxy resin obtained by reacting a mixture of a 1,1-bis(2,7-dihydroxy-1-naphthyl)alkane, a 1-(2,7-dihydroxy-1-naphthyl)-1-(2-hydroxy-1-naphthyl)alkane, and a 1,1-bis(2-hydroxy-1-naphthyl)alkane with an epihalohydrin and a curing agent.

4. An epoxy resin composition as claimed in claim 3, wherein said 1,1-bis(2,7-dihydroxy-1-naphthyl)alkane is selected from the group consisting of 1,1-bis(2,7-dihydroxy-1-naphthyl)methane, 1,1-bis(2,7-dihydroxy-1-naphthyl)ethane, 1,1-bis(2,7-dihydroxy-1-naphthyl)propane, 1,1-bis(2,7-dihydroxy-1-naphthyl butane, 1,1-bis(2,7-dihydroxy-1-naphthyl)-1-phenylmethane, and 1,1-bis(2,7-dihydroxy-1-naphthyl)-1-(4-hydroxyphenyl methane, said 1-(2,7-dihydroxy-1-naphthyl)alkane is selected from the group consisting of 1-(2,7-dihydroxy-1-naphthyl)-1-(2-hydroxy-1-naphthyl)methane, 1-(2,7-dihydroxy-1-naphthyl)-1-(2-hydroxy-1-naphthyl)ethane, 1-(2,7-dihydroxy-1-naphthyl)-1-(2-hydroxy-1-naphthyl)propane, 1-(2,7-dihydroxy-1-naphthyl)-1-(2-hydroxy-1-naphthyl)butane, 1-(2,7-dihydroxy-1-naphthyl)-1-(2-hydroxy-1-naphthyl)-1-phenylmethane, and 1-(2,7-dihydroxy-1-naphthyl)-1-(2-hydroxy-1-naphthyl)-1-(4-hydroxyphenyl)methane, and said 1,1-bis(2-hydroxy-1-naphthyl)alkane is selected from the group consisting of 1,1-bis(2-hydroxy-1-naphthyl)methane, 1,1-bis(2-hydroxy-1-naphthyl)ethane, 1,1-bis(2-hydroxy-1-naphthyl)propane, 1,1-bis(2-hydroxy-1-naphthyl)butane, 1,1-bis(2-hydroxy-1-naphthyl)1-(4-hydroxyphenyl)methane.

5. An epoxy resin composition as claimed in claim 3, wherein said mixture of a 1,1-bis(2,7-dihydroxy-1-naphthyl)alkane, a 1,1-bis(2,7-dihydroxy-1-naphthyl)-1-(2-hydroxy-1-naphthyl)alkane, and a 1,1-bis(2-hydroxy-1-naphthyl)alkane is a reaction product between a mixture of 2,7-dihydroxynaphthalene and β-naphthol and an aldehyde.

6. An epoxy resin composition as claimed in claim 5, wherein said aldehyde is selected from the group consisting of formaldehyde, acetaldehyde, propyl aldehyde, butyl aldehyde, benzaldehyde, and p-hydroxybenzaldehyde.

* * * * *